US006615155B2

United States Patent
Gilboa

(10) Patent No.: US 6,615,155 B2
(45) Date of Patent: Sep. 2, 2003

(54) OBJECT TRACKING USING A SINGLE SENSOR OR A PAIR OF SENSORS

(75) Inventor: Pinhas Gilboa, Haifa (IL)

(73) Assignee: Super Dimension Ltd., Herzelia (IL)

( * ) Notice: Subject to any disclaimer, the term of this patent is extended or adjusted under 35 U.S.C. 154(b) by 152 days.

(21) Appl. No.: 09/819,676

(22) Filed: Mar. 29, 2001

(65) Prior Publication Data
US 2002/0062203 A1 May 23, 2002

Related U.S. Application Data
(60) Provisional application No. 60/188,025, filed on Mar. 9, 2000.

(51) Int. Cl.[7] ............... G01B 7/004; H01F 5/00; A61B 5/05
(52) U.S. Cl. ............... 702/150; 324/207.17; 342/463; 600/409; 600/424
(58) Field of Search ............... 324/207.11, 207.13, 324/207.17, 207.22; 342/463; 600/407, 409, 424, 463; 702/150

(56) References Cited

U.S. PATENT DOCUMENTS

| 3,868,565 A | 2/1975 | Kuipers | 324/207.26 |
|---|---|---|---|
| 3,983,474 A | 9/1976 | Kuipers | 324/207.18 |
| 4,017,858 A | 4/1977 | Kuipers | 342/350 |
| 4,054,881 A | 10/1977 | Raab | 342/448 |
| 4,287,809 A | 9/1981 | Egli | 89/41.21 |
| 4,314,251 A | 2/1982 | Raab | 342/463 |
| 4,328,548 A | 5/1982 | Crow | 701/207 |
| 4,346,384 A | 8/1982 | Raab | 342/451 |
| 4,394,831 A | 7/1983 | Egli | 89/41.19 |
| 4,396,885 A | 8/1983 | Constant | 324/207.18 |
| 4,613,866 A | 9/1986 | Blood | 342/448 |
| 4,710,708 A | 12/1987 | Rorden | 324/207.26 |
| 4,737,794 A | 4/1988 | Jones | 342/448 |
| 4,742,356 A | 5/1988 | Kuipers | 342/448 |
| 4,849,692 A | 7/1989 | Blood | 324/207.26 |
| 5,307,072 A | 4/1994 | Jones, Jr. | 342/147 |
| 5,377,678 A | 1/1995 | Dumoulin et al. | 600/424 |
| 5,600,330 A | 2/1997 | Blood | 342/463 |
| 5,646,525 A | 7/1997 | Gilboa | 324/207.17 |
| 5,729,129 A | 3/1998 | Acker | 324/207.12 |
| 5,752,513 A | 5/1998 | Acker | 600/424 |

FOREIGN PATENT DOCUMENTS

| EP | 922966 | 6/1999 |
|---|---|---|
| WO | WO94/04938 | 3/1994 |
| WO | WO96/05768 | 2/1996 |
| WO | WO 99/32033 | 7/1999 |

Primary Examiner—Kamini Shah
(74) Attorney, Agent, or Firm—Mark M. Friedman

(57) ABSTRACT

A method and system for tracking a moving object. The object is provided with one or more single-component sensors of a vector field. Generators of the vector field also are provided. Parameters of equations that relate the generated fields, as measured by the sensors, to the position of the object, but not to the orientation of the object, are determined either empirically or theoretically. These equations are solved to determine the position of the object without having to determine the orientation of the object. The scope of the invention also includes a helical guide wire wherein are integrally included one or more single-component sensors of a quasistatic magnetic field.

64 Claims, 11 Drawing Sheets

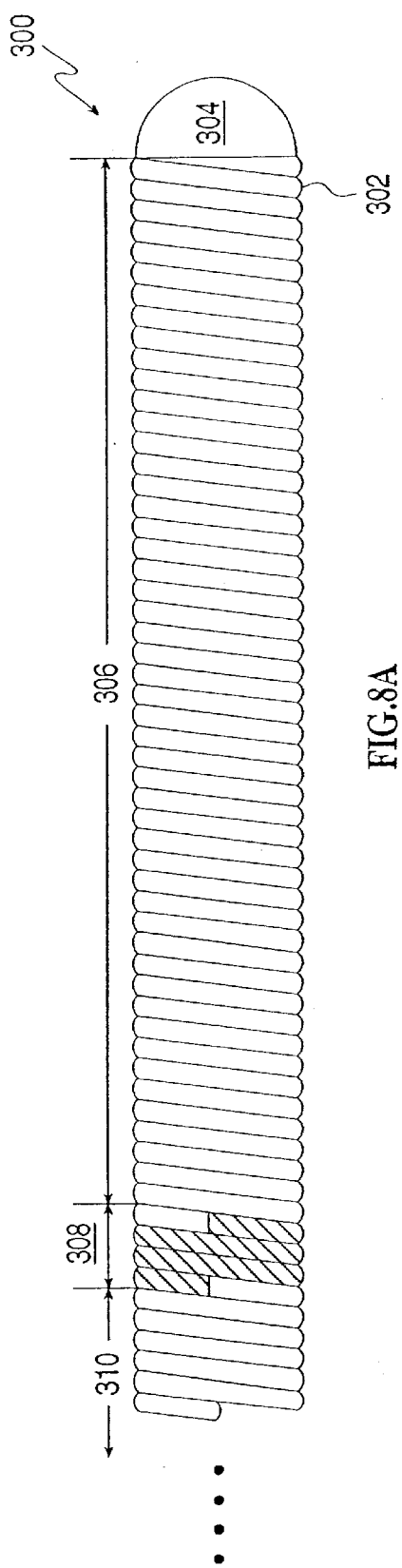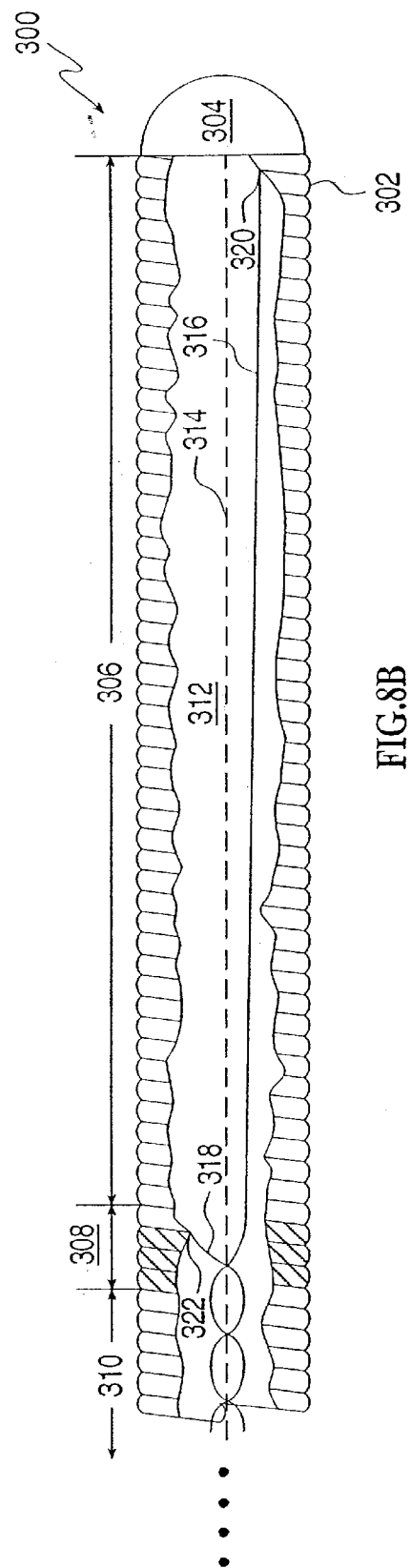

OBJECT TRACKING USING A SINGLE SENSOR OR A PAIR OF SENSORS

This application claims the benefit of Provisional Application No. 60/188,025, filed Mar. 9, 2000.

FIELD AND BACKGROUND OF THE INVENTION

The present invention relates to vector field tracking of a moving object and, more particularly, to a method of tracking a moving object with a small number (one or two) of vector field sensors attached thereto.

It is known to track the position and orientation of a moving object with respect to a fixed frame of reference, by equipping the moving object with a transmitter that transmits low frequency electromagnetic radiation, placing a receiver in a known and fixed position in the fixed frame of reference, and inferring the continuously changing position and orientation of the object from signals transmitted by the transmitter and received by the receiver. Equivalently, by the principle of reciprocity, the moving object is equipped with a receiver, and a transmitter is placed in a known and fixed position in the fixed frame of reference. Alternatively, the moving object is equipped with a generator that generates a static magnetic field, and a magnetometer is substituted for the receiver. Again, by the principle of reciprocity, the moving object may be equipped with a magnetometer, and a generator of a static magnetic field may be placed in a known and fixed position in the fixed frame of reference. Typically, the transmitter includes three orthogonal magnetic dipole transmitting antennas; the receiver includes three orthogonal magnetic dipole receiving sensors; and the transmitter and the receiver are sufficiently close to each other, and the frequencies of the signals are sufficiently low, that the signals are near field signals. Such orthogonal transmitting antennas also can be used to generate a static magnetic field; the magnetometer in that case typically is a three component vector magnetometer. Representative prior art patents in this field include U.S. Pat. No. 3,868,565, U.S. Pat. No. 3,983,474, U.S. Pat. No. 4,017,858 and U.S. Pat. No. 4,742,356, to Kuipers; U.S. Pat. No. 4,054,881, U.S. Pat. No. 4,314,251 and U.S. Pat. No. 4,346,384, to Raab; U.S. Pat. No. 4,287,809 and U.S. Pat. No. 4,394,831, to Egli et al.; U.S. Pat. No. 4,328,548, to Crow et al.; U.S. Pat. No. 4,396,885, to Constant; U.S. Pat. No. 4,613,866 and U.S. Pat. No. 4,849,692, to Blood; U.S. Pat. No. 4,737,794 and U.S. Pat. No. 5,307,072, to Jones; and U.S. Pat. No. 5,646,525, to Gilboa.

For the most part, these patents assume point dipole transmitters/generators and, in the electromagnetic embodiments, point dipole receivers. Jones (U.S. Pat. No. 4,737,794 and U.S. Pat. No. 5,307,072) and Egli et al. (U.S. Pat. No. 4,394,831) discuss multipole corrections to the basic point dipole model. Blood (U.S. Pat. No. 5,600,330), Acker et al. (U.S. Pat. No. 5,752,513) and Ben-Haim et al. (WO 96/05768) also treat spatially extended transmitters/receivers.

Also, for the most part, the prior art in this field requires a simultaneous determination of both the position and the orientation of the moving object. Acker, in U.S. Pat. No. 5,729,129, shows how the theoretical expressions describing the fields produced by point dipoles can be used to solve for the position and orientation of the moving object, given any combination of point dipole transmitters and point dipole receivers that provide enough equations to solve for all six unknowns (three position coordinates and three orientation angles). Similar theoretical expressions for the fields produced by spatially extended generators and transmitters can be obtained based on Ampere's law (Blood, U.S. Pat. No. 5,600,330) or the Biot-Savart law (Gilboa et al., EP 922, 966). Blood also shows how the position alone of the object can be obtained, without also computing the orientation of the object, in the case of three magnetic field generators and a three-component magnetometer. Gilboa et al., EP 922,966, provide expressions for the three position coordinates and the three orientation angles of a three component receiver in terms of signals received from three spatially extended transmitters.

There are circumstances in which the restricted space, in which the moving object moves, imposes the constraint that the moving object can be equipped with only one transmitter component or only one receiver component. For example, a borehole logging tool must be slender enough to move through a borehole, and a catheter must be slender enough to move through a blood vessel. In both these cases, there is room in the object for only one transmitter or receiver coil, aligned with the longitudinal axis of the object. Rorden et al. (U.S. Pat. No. 4,710,708), Bladen et al. (WO 94/04938), Dumoulin et al. (U.S. Pat. No. 5,377,678) and Schneider (U.S. Pat. No. 6,073,043) all show how to derive the combined position and orientation of the object from signals transmitted by a single component transmitter on board the object or from signals received by a single component receiver on board the object. Bladen et al. are of particular note as showing, in the case of point dipole transmitters and a single component receiver, how an imprecise estimate of the object's position can be calculated independently of the object's orientation; this imprecise estimate then is used as an initial position estimate in an iterative combined calculation of both position and orientation. Nevertheless, the prior art does not teach how the exact position of a single-component receiver can be obtained without also computing the orientation of the receiver. Furthermore, even in the case of a three component receiver and a three component transmitter, algorithms such as Blood's for determining only the position of the receiver presuppose the availability of theoretical expressions for the fields generated by the transmitters.

SUMMARY OF THE INVENTION

According to the present invention there is provided a method of tracking an object that moves in three dimensions, including the steps of: (a) providing the object with at least one vector field component sensor for measuring a respective component of a vector field; (b) for each at least one vector field component sensor, empirically determining parameters of a set of equations that relate the respective component only to a position of the object with respect to a reference frame; (c) providing a plurality of vector field generators for generating respective instances of the vector field, each generator having a fixed respective position in the reference frame; (d) for each generator: (i) generating the respective instance of the vector field, and (i) for each at least one sensor, measuring the respective component of the respective instance of the vector field; and (e) solving the set of equations for the position of the object.

According to the present invention there is provided a method of tracking an object that moves in three dimensions, including the steps of: (a) providing the object with at most two vector field component sensors for measuring respective components of a vector field; (b) for each at most two vector field component sensors, determining parameters of a set of equations that relate the respective component only to a position of the object with respect to a reference frame; (c) providing at least three vector field generators for generating respective instances of the vector field, each generator having a fixed respective position in the reference frame; (d) for each generator: (i) generating the respective instance of the vector field, and (i) for each at most two sensors, measuring the respective component of the respective instance of the vector field; and (e) solving the set of equations for the position of the object.

According to the present invention there is provided a system for tracking an object that moves in three dimensions, including: (a) at least one vector field component sensor, associated with the object, for measuring a respective component of a vector field; (b) a processor for solving a set of equations that relate, for each at least one sensor, the respective component of the vector field only to a position of the object with respect to a reference frame; (c) a memory for storing empirically determined parameters of the equations; and (d) a plurality of vector field generators, having fixed respective positions in the reference frame, for generating respective instances of the vector field.

According to the present invention there is provided a system for tracking an object that moves in three dimensions, including: (a) at most two vector field component sensors, associated with the object, for measuring respective components of a vector field; (b) a processor for solving a set of equations that relate, for each sensor, the respective component of the vector field only to a position of the object with respect to a reference frame; (c) a memory for storing parameters of the equations; and (d) at least three vector field generators, having fixed respective positions in the reference frame, for generating respective instances of the vector field.

According to the present invention there is provided a guide wire, including:

(a) a substantially helical distal portion including at least one electrically conducting section; and (b) a substantially helical, electrically insulating medial portion in tandem with the distal portion.

According to the present invention there is provided a method of tracking an object that moves in three dimensions, including the steps of: (a) providing the object with at least one vector field component sensor for measuring a respective component of a vector field; (b) empirically determining a rotationally invariant operator that relates the at least one respective component to a position of the object with respect to a reference frame; (c) providing a plurality of vector field generators for generating respective instances of the vector field, each generator having a fixed respective position in the reference frame; (d) for each generator: (i) generating the respective instance of the vector field, and (i) for each at least one sensor, measuring the respective component of the respective instance of the vector field; and (e) computing the position of the object, using the operator.

According to the present invention there is provided a method of tracking an object that moves in three dimensions, including the steps of: (a) providing the object with at most two vector field component sensors for measuring respective components of a vector field; (b) determining a rotationally invariant operator that relates the at most two respective components to a position of the object with respect to a reference frame; (c) providing at least three vector field generators for generating respective instances of the vector field, each generator having a fixed respective position in the reference frame; (d) for each generator: (i) generating the respective instance of the vector field, and (i) for each at most two sensors, measuring the respective component of the respective instance of the vector field; and (e) computing the position of the object, using the operator.

According to the present invention there is provided a system for tracking an object that moves in three dimensions, including: (a) at least one vector field component sensor, associated with the object, for measuring a respective component of a vector field; (b) a memory for storing an empirically determined, rotationally invariant operator that relates the at least one respective component of the vector field to a position of the object with respect to a reference frame; (c) a processor for computing the position, using the operator; and (d) a plurality of vector field generators, having fixed respective positions in the reference frame, for generating respective instances of the vector field.

According to the present invention there is provided a system for tracking an object that moves in three dimensions, including: (a) at most two vector field component sensors, associated with the object, for measuring respective components of a vector field; (b) a memory for storing a rotationally invariant operator that relates the at most two respective components of the vector field to a position of the object with respect to a reference frame; (c) a processor for computing the position, using the operator; and (d) at least three vector field generators, having fixed respective positions in the reference frame, for generating respective instances of the vector field.

According to the present invention there is provided a method of tracking an object that moves in three dimensions, including the steps of: (a) providing the object with at most two vector field component sensors for measuring respective components of a vector field; (b) for each at most two vector field component sensors, determining parameters of a set of equations that relate the respective component to a position of the object with respect to a reference frame, independent of an orientation of the object; (c) providing at least three vector field generators for generating respective instances of the vector field, each generator having a fixed respective position in the reference frame; (d) for each generator: (i) generating the respective instance of the vector field, and (i) for each at most two sensors, measuring the respective component of the respective instance of the vector field; and (e) solving the set of equations for the position of the object.

According to the present invention there is provided a system for tracking an object that moves in three dimensions, including: (a) at most two vector field component sensors, associated with the object, for measuring respective components of a vector field; (b) a processor for solving a set of equations that relate, for each sensor, the respective component of the vector field to a position of the object with respect to a reference frame, independent of an orientation of the object; (c) a memory for storing parameters of the equations; and (d) at least three vector field generators, having fixed respective positions in the reference frame, for generating respective instances of the vector field.

The vector field of the present invention may be any suitable vector field, for example, an elastic force field. Nevertheless, the present invention is directed primarily at the use of static magnetic fields and quasistatic electromagnetic fields, and the examples presented herein all are static magnetic fields or quasistatic electromagnetic fields. The term "magnetic field" as used herein encompasses both a static (DC) magnetic field and the magnetic component of a time varying, preferably quasistatic, electromagnetic field. In the case of a quasistatic magnetic field, the sensor preferably is based on at least one loop of an electrical conductor, for example, a coil of electrically conducting wire. In the case of a static magnetic field, the sensor preferably is a single component magnetometer, based, for example, on a generally planar magnetically sensitive film, such as a magneto-resistive film or a Hall effect sensing film, as described in WO 95/09562. Other suitable magnetometers include magneto-optical sensors, flux gate magnetometers and Hall effect diodes.

The present invention is based on the discovery that the responses of a single magnetic field component sensor to a suitable set of independent generators of a static or quasistatic magnetic field can be formulated in a set of equations in which the positional coordinates of the sensor appear but in which the orientational angles of the sensor do not appear. Thus, these equations relate the component of the respective fields, generated by the generators, that is measured by the sensor only to the position of the sensor and not to the orientation of the sensor. In general, the generators include radiators of respective instances of the vector field. These radiators may be spatially extended. In the present context, a "spatially extended" radiator is a radiator that is too large relative to the sensor, and/or too close to the sensor, to be treated as a point radiator. In particular, a "spatially extended" radiator is a radiator that is too large relative to the sensor, and/or too close to the sensor, to be treated as a point dipole radiator. In the usual case of the vector field being a static or quasistatic magnetic field, each radiator preferably includes one or more loops of an electrical conductor.

The equations are formulated in terms of certain parameters. If three or more sensors are used, then the parameters are determined empirically. If only one or two sensors are used, then the parameters are determined either theoretically or experimentally. If two sensors are used, then at least three generators are used. If only one sensor is used, then at least five generators are used.

Optionally, after the position of the object is determined, the orientation of the object is determined too.

As will be readily understood by those skilled in the art, the equations of the present invention are mathematically equivalent to a rotationally invariant operator that relates the field component(s) measured by the sensor(s) to the position of the object.

The scope of the present invention also includes a system for implementing the method of the present invention. The system includes one or more vector field sensors associated with the object, a suitable number of vector field generators, a memory for storing the parameters of the equations, and a processor for solving the equations.

In one embodiment of the system of the present invention, the one or more vector field sensors are tandem sections of the distal portion of a guide wire. Specifically, the guide wire is configured as a helical coil of electrically conducting and insulating materials. The vector field sensors are electrically conducting sections of the coil. If there are two or more vector field sensors, successive vector field sensors are separated by electrically insulating sections of the coil. The remainder of the coil includes an electrically insulating medial portion and an electrically conducting proximal portion.

The helical coil defines an axial channel. A respective first electrically conducting wire is electrically coupled to a distal end of each vector field sensor. A respective second electrically conducting wire is electrically coupled to a proximal end of each vector field sensor. The electrically conducting wires extend through the axial channel, substantially parallel to the channel axis.

In another embodiment of the system of the present invention, two vector field sensors are mounted in the distal portion of a guide wire. One of the vector field sensors is parallel to the longitudinal axis of the guide wire. The other vector field sensor is perpendicular to the longitudinal axis of the guide wire.

BRIEF DESCRIPTION OF THE DRAWINGS

The invention is herein described, by way of example only, with reference to the accompanying drawings, wherein:

FIGS. 8A, 8B, 9 and 10 illustrate guide wires of the present invention.

THEORY

Figure 1:
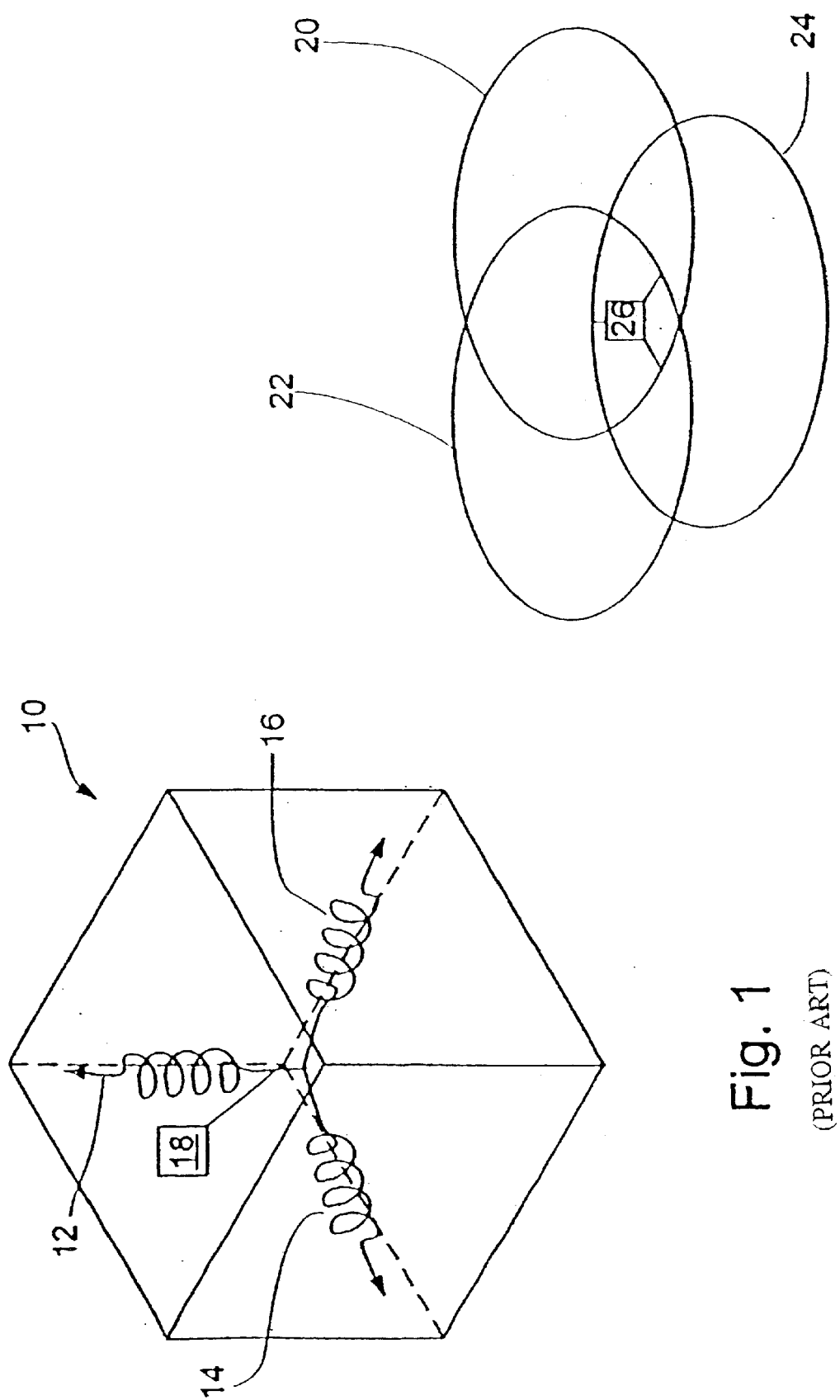
FIG. 1 is a schematic depiction of prior art hardware that is useful in explaining the theory of the present invention.

The theory of the present invention is most conveniently explained with reference to FIG. 1 of Gilboa et al., EP 922,966, which is reproduced herein as FIG. 1. FIG. 1 shows a moving object 10 provided with three orthogonal sensor coils 12, 14 and 16 of electrically conducting wire, electrically coupled to reception circuitry 18. Also provided are three independent transmitters of quasistatic electromagnetic radiation, each of which includes a respective spatially extended antenna 20, 22 or 24. By "independent" generators is meant that the field generated by one generator can not be expressed as a linear combination of the fields generated by the other two generators. Transmission circuitry 26 includes the remainder of the three transmitters, as well as circuitry for synchronizing the transmissions. (Note that the roles of transmitters and receivers have been interchanged relative to the description in Gilboa et al., EP 922,966; this is allowed by the principle of reciprocity.) Each antenna 20, 22 or 24 radiates a respective quasistatic electromagnetic field, the magnetic component of which excites a respective electrical current in each of sensor coils 12, 14 and 16. It is assumed that sensor coils 12, 14 and 16 are sufficiently small that the gradient of the magnetic field at sensor coils 12, 14 and 16 is spatially uniform. This magnetic field is referred to in the subsequent discussion as the magnetic field "at" object 10.

Designate the vectorial magnetic field radiated by antenna 20 as $\underline{B}_1(\underline{r})$, the vectorial magnetic field radiated by antenna 22 as $\underline{B}_2(\underline{r})$, and the vectorial magnetic field radiated by antenna 24 as $\underline{B}_3(\underline{r})$. These fields are functions of a position vector $\underline{r}$ whose Cartesian components (in the frame of reference defined by antennas 20, 22 and 24) are (x,y,z). The corresponding Cartesian components of $\underline{B}_1$ are $(B_{1x}, B_{1y}, B_{1z})$, and similarly for $\underline{B}_2$ and $\underline{B}_3$. Define a 3×3 matrix B whose three columns are the vectorial magnetic fields $\underline{B}_1$, $\underline{B}_2$ and $\underline{B}_3$. In general, the signals received by reception circuitry 18 can be represented as another 3×3 matrix S that is related to B by a 3×3 rotation matrix R and a scale factor k that is independent of position $\underline{r}$:

$$S = kRB \quad (1)$$

(Strictly speaking, in the quasistatic case, both S and B have an exp(i$\omega$t) dependence on time t, where i is the square root of –1 and $\omega$ is the angular frequency of the magnetic field. For notational simplicity, this time dependence has been suppressed.) The rotation matrix R accounts for sensor coils 12, 14 and 16 in generally not being aligned with the Cartesian axis of the reference frame. In the special case of coil 12 pointing in the +x-direction, coil 14 pointing in the +y direction and coil 16 pointing in the +z direction, R is an identity matrix.

Now remove sensor coils 14 and 16 from object 10, so that object 10 is tracked using only sensor coil 12. The three signals received by reception circuitry 18 from antennas 20, 22 and 24 are the elements of the first row of S, i.e., a row vector v whose elements are $v_1 = S_{11}$, $v_2 = S_{12}$ and $v_3 = S_{13}$. $\underline{v}$ is obtained from S by left-multiplying S by the row vector (1,0,0). In general, the matrix B is non-singular. Right-multiplying $\underline{v}$ by $B^{-1}k^{-1}$ and taking the magnitude of the resulting row vector gives $$|\underline{v}B^{-1}k^{-1}| = |(1,0,0)kRBB^{-1}| = |(R_{11},R_{12},R_{13})| = 1 \quad (2)$$

Now consider the three vectors $\underline{v}_a$, $\underline{v}_b$ and $\underline{v}_c$ of signals received by reception circuitry 18, at one particular position r and orientation of object 10, in response to the magnetic fields generated by three independent sets of transmitting antennas such as antennas 20, 22 and 24. By "independent" sets is meant that the magnetic field matrix B generated by one set can not be expressed as a linear combination of the magnetic field matrices B generated by the other two sets. An equation such as equation (1) can be defined for each of the three independent sets:

$$\underline{v}_a = k(R_{11},R_{12},R_{13})B_a \quad (3a)$$

$$\underline{v}_b = k(R_{11},R_{12},R_{13})B_b \quad (3a)$$

$$\underline{v}_c = k(R_{11},R_{12},R_{13})B_c \quad (3a)$$

All three equations (3) share the same factor k, which is a property of reception circuitry 18, and the same first row of the same rotation matrix R, which expresses the orientation of object 10. Therefore, there are three independent equations, $$|\underline{v}_a B_a^{-1} k^{-1}| = 1 \quad (4a)$$

$$|\underline{v}_b B_b^{-1} k^{-1}| = 1 \quad (4b)$$

$$|\underline{v}_c B_c^{-1} k^{-1}| = 1 \quad (4c)$$

for the three unknown components of position $\underline{r}$. Given the measured signals $\underline{v}_a$, $\underline{v}_b$ and $\underline{v}_c$, the overall scale factor k, and also matrices $B_a$, $B_b$ and $B_c$ as algebraic functions of $\underline{r}$, equations (4) may be solved iteratively for the position of object 10.

As is explained in more detail below, the preferred representation of $B^{-1}k^{-1}$ is as polynomials in x, y and z.

With the position $\underline{r}$ of object 10 determined, the orientation of object 10 may be determined. The elements of R generally, and the three elements $R_{11}$, $R_{12}$ and $R_{13}$ of the first row of R in particular, are trigonometric functions of the angles that define the orientation of object 18. Equations (3) thus constitute three independent equations for these orientation angles.

Figure 2:
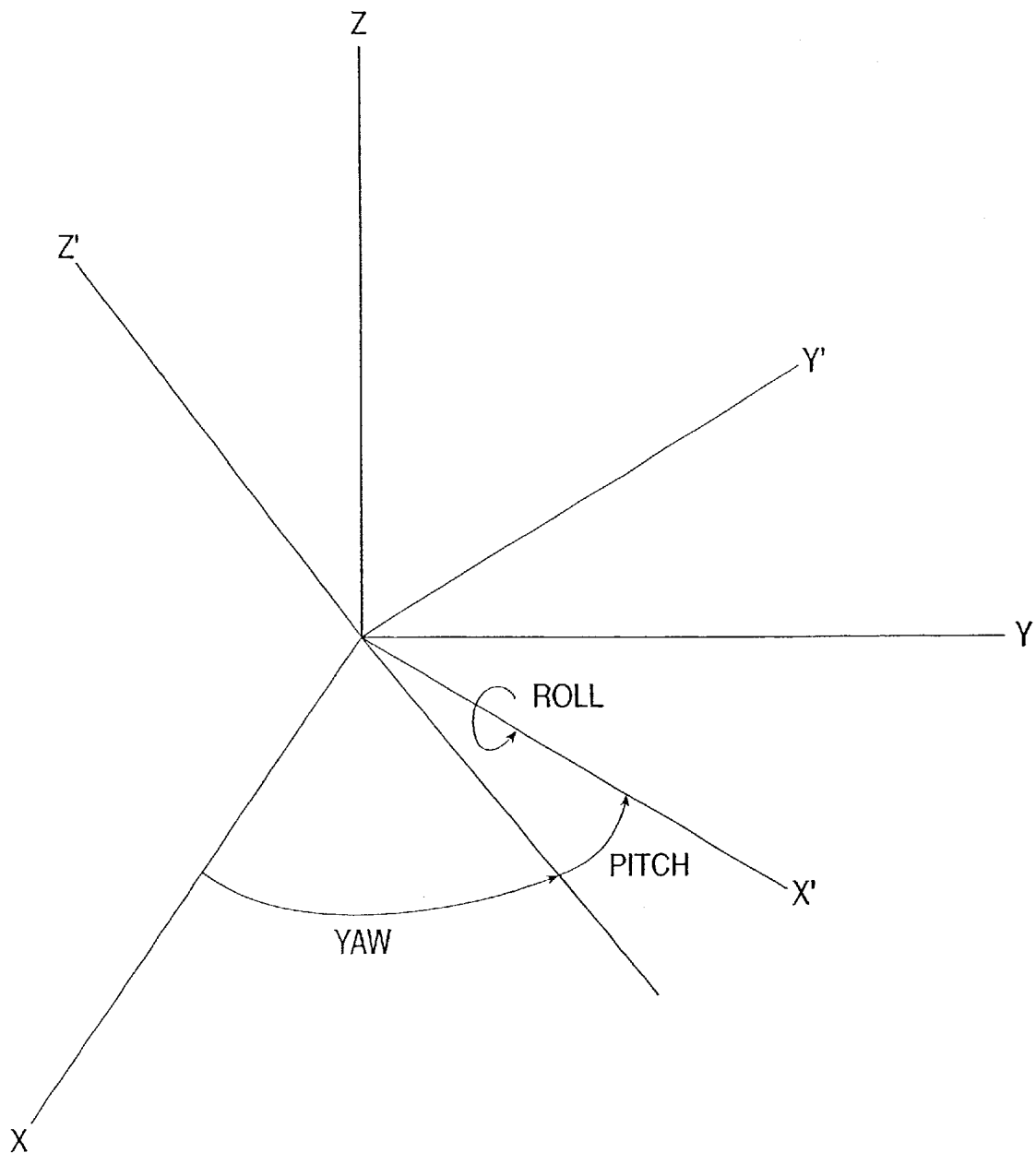
FIG. 2 illustrates one convention for defining orientation angles.

There are several conventions for defining these orientation angles. One such convention is illustrated in FIG. 2, which shows the local Cartesian coordinate axes (x',y',z') of object 10 rotated with respect to the Cartesian coordinate axes (x,y,z) of the frame of reference. YAW is the angle between the x-axis and the projection on the xy plane of the x' axis. PITCH is the angle between the xy plane and the x' axis. ROLL is the rotation of the y' and z' axes about the x' axis. Note that with only one sensor coil present in object 10, only two of these angles can be determined, as can be seen by considering the case of sensor coil 12 directed along the x' axis: the signals received by reception circuitry 18 then are independent of ROLL.

Now consider the case of removing only sensor coil 16 from object 10, and generalize to the case in which there is an angle $\alpha$, not necessarily equal to 90°, between the magnetic field components sensed by sensor coils 12 and 14. In a transparent change of notation, the signal received by reception circuitry 18 from sensor coil 12 is $$\underline{v}_1 = k(R_{11},R_{12},R_{13})B \quad (5a)$$

and the similar signal received by reception circuitry 18 from sensor coil 14 is $$\underline{v}_{11} = k(R'_{11},R'_{12},R'_{13})B \quad (5b)$$

where $(R'_{11},R'_{12},R'_{13})$ is the first row of a rotation matrix R' that is related to R by the rotation that transforms the direction in which sensor coil 12 points into the direction in which sensor coil 14 points, so that $R_{11}$, $R_{12}$, $R_{13}$, $R'_{11}$, $R'_{12}$ and $R'_{13}$ all are trigonometric functions of the same YAW, PITCH and ROLL of object 10. Now only one set of three transmitting antennas is needed. The first of three equations for $\underline{r}$ is obtained by right-multiplying $\underline{v}_1$ by $B^{-1}k^{-1}$ as before and taking the magnitude of the resulting row vector:

$$|\underline{v}_1 B^{-1} k^{-1}| = 1 \quad (6a)$$

The second equation is obtained similarly from $\underline{v}_{11}$:

$$|\underline{v}_{11} B^{-1} k^{-1}| = 1 \quad (6b)$$

The third equation is obtained from the dot product of $(R_{11},R_{12},R_{13})$ and $(R'_{11},R'_{12},R'_{13})$:

$$(\underline{v}_1 B^{-1} k^{-1}) \cdot (\underline{v}_{11} B^{-1} k^{-1}) = (R_{11},R_{12},R_{13}) \cdot (R'_{11},R'_{12},R'_{13}) = \cos \alpha \quad (6c)$$

Solving equations (6) as before for $\underline{r}$ gives the position of object 10. With the position of object 10 determined, equations (5a), (5b) and (6c) provide three equations for the three orientation angles of object 10. In this case, however, all three orientation angles may be found.

The solution of equations (4) or of equations (6) for the position of object 10 presupposes the availability of $B_a$, $B_b$ and $B_c$, (in the case of one sensor coil on object 10), or the availability of B (in the case of two sensor coils on object 10) as algebraic functions of x, y and z. These algebraic functions are obtained in a calibration procedure discussed below.

This theoretical development has been presented in terms of sensor coils 12 and 14 used to sense a quasistatic magnetic field. The same derivation applies to one-component or two-component vector magnetometers used to sense a static magnetic field.

DESCRIPTION OF THE PREFERRED EMBODIMENTS

The present invention is of a method and system for tracking a moving object. Specifically, the present invention can be used to determine the position of a moving object without having to determine the orientation of the object, and with the use of only one or two vector field sensors on the object.

The principles and operation of vector field tracking according to the present invention may be better understood with reference to the drawings and the accompanying description.

Figure 3:
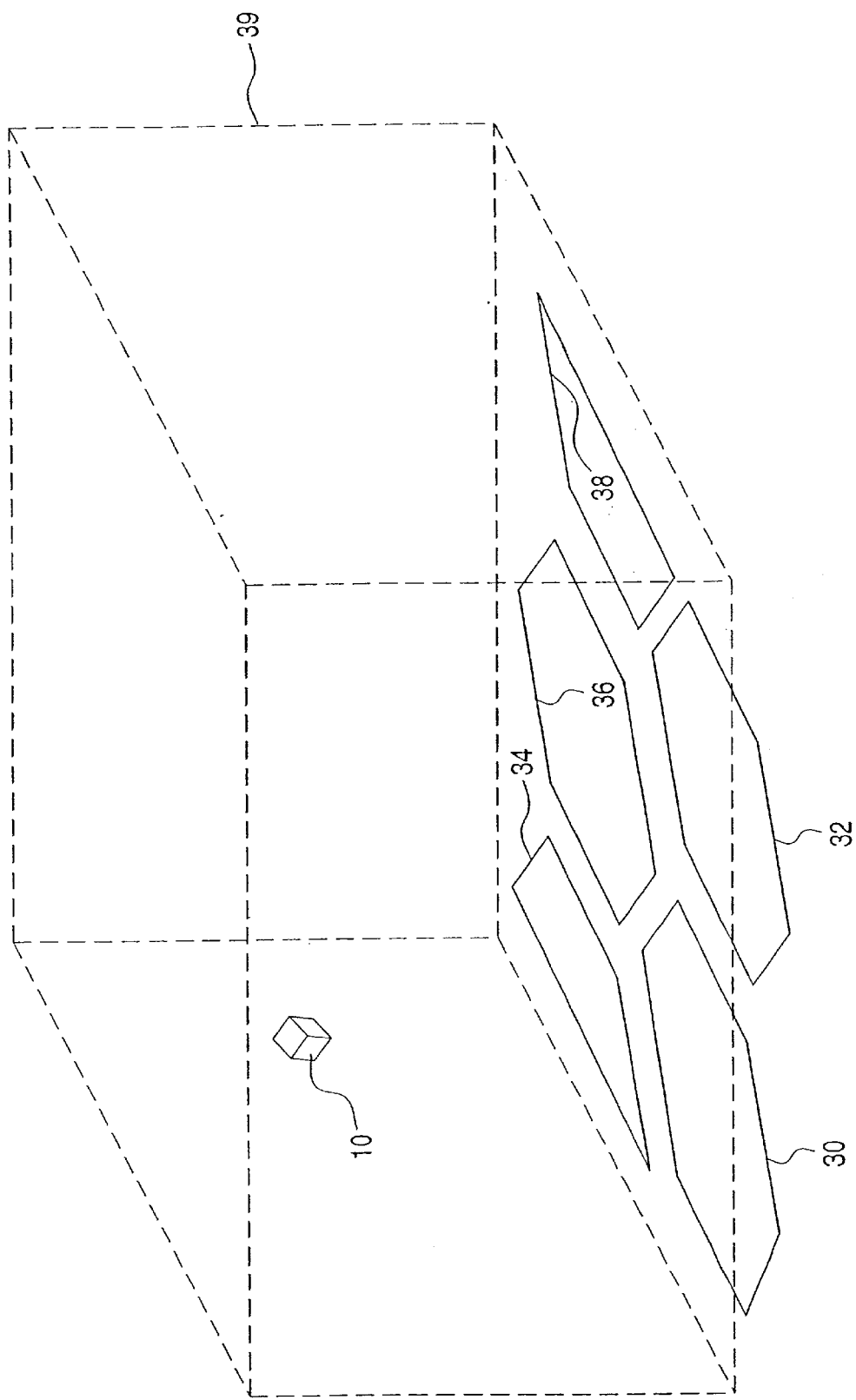
FIG. 3 shows a minimal set of radiators for tracking a moving object with a single sensor.

Returning now to the drawings, FIG. 3 illustrates the minimal set of radiators needed to implement the present invention in the case of a single magnetic field component sensor on object 10: five planar loop antennas 30, 32, 34, 36 and 38. In this example, antennas 30, 32, 34, 36 and 38 are nonoverlapping and coplanar. Object 10 moves in the space 39 adjacent to antennas 30, 32, 34, 36 and 38, off to one side of the common plane of antennas 30, 32, 34, 36 and 38, so that antennas 30, 32, 34, 36 and 38 all are spatially extended relative to object 10. The first independent set (set a) of transmitting antennas consists of antennas 30, 34 and 36. The second independent set (set b) of transmitting antennas consists of antennas 32, 36 and 38. The third set (set c) of transmitting antennas consists of antennas 34, 36 and 38.

Figure 4:
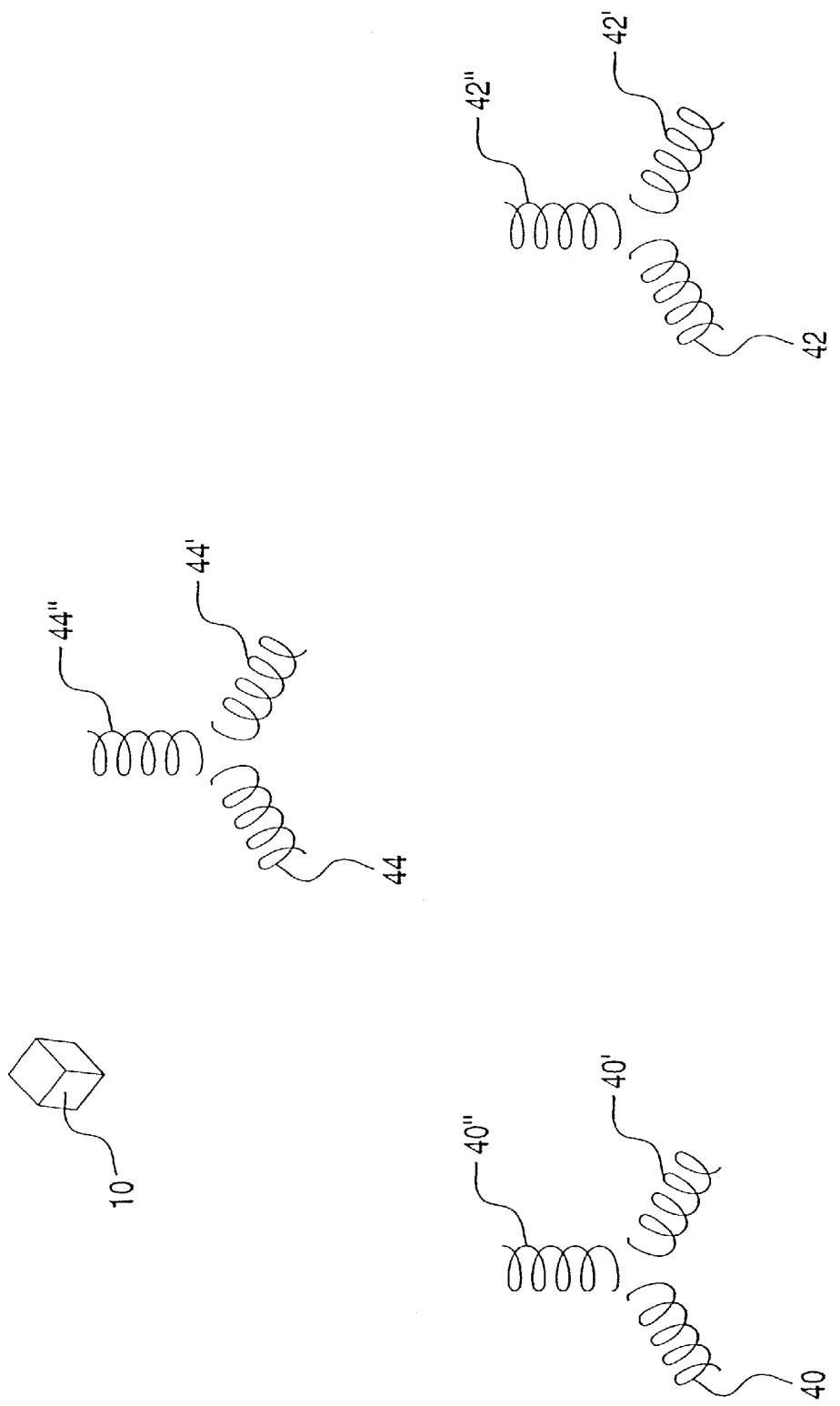
FIG. 4 shows another set of radiators for tracking a moving object with a single sensor.

Although five transmitting antennas suffice to provide three independent sets of transmitting antennas, it is preferred to use sets of transmitting antennas that do not share transmitting antennas, in order to obtain better-conditioned equations (4). FIG. 4 shows one preferred layout of transmitting antennas, in three sets of orthogonal coils. Set a includes coils 40, 40' and 40". Set b includes coils 42, 42' and 42". Set c includes coils 44, 44' and 44".

As noted above, in the case of a single magnetic field sensor on object 10, the method of the present invention presupposes the availability of algebraic expressions for the matrices $B_a$, $B_b$ and $B_c$ as functions of position $\underline{r}$. One way to obtain these algebraic expressions is theoretical, as in the prior art of Acker (U.S. Pat. No. 5,729,129), Blood (U.S. Pat. No. 5,600,330) and Gilboa et al. (EP 922,966). Specifically, spatially localized transmitting antennas, such as the transmitting antennas of FIG. 4, are modeled as point dipoles; and spatially extended transmitting antennas, such as the transmitting antennas of FIG. 3, are modeled using Ampere's law for static magnetic fields and the Biot-Savart law for quasistatic magnetic fields. The constant k is obtained by measuring the signals received by reception circuitry 18 at one standard position and one standard orientation of object 10 and by comparing these signals to the theoretically predicted fields at that position and orientation. Note that in the present context this calibration of the method of the present invention is considered a theoretical calibration, despite the single empirical set of measurements needed to obtain k, because the functional forms of the magnetic fields, as functions of position $\underline{r}$, are obtained theoretically.

With functional forms for the elements of matrices $B_a$, $B_b$ and $B_c$, as functions of $\underline{r}$, having been determined, and with k having been measured, values of the inverse matrices $M_a = B_a^{-1} k^{-1}$, $M_b = B_b^{-1} k^{-1}$ and $M_c = B_c^{-1} k^{-1}$ are computed at a set of N calibration points $\{\underline{r}_n\}$. Values of these matrices are interpolated elsewhere in space by standard numerical methods. Preferably, each component M of each inverse matrix is expressed as a parametrized function of position coordinates (x,y,z). Many such functional forms are known in the art of numerical analysis, for example, rational functions and continued fractions; but the preferred functional form is a polynomial:

$$M(x, y, z) = \sum_{j,k,l \geq 0} C_{jkl} x^j y^k z^l \quad (7)$$

The parameters in equation (7) are the polynomial coefficients $C_{jkl}$. If N is greater than the number of coefficients $C_{jkl}$, then the N equations $$M(x_n, y_n, z_n) = \sum_{j,k,l \geq 0} C_{jkl} x_n^j y_n^k z_n^l \quad (7)$$

constitute a set of overdetermined equations for the coefficients $C_{jkl}$. These equations may be solved by standard linear least squares methods. The optimum number of coefficients $C_{jkl}$ can be determined easily by those skilled in the art in any given case. Higher degree polynomials give higher numerical accuracy, at the expense of having to calibrate at more points $\underline{r}_n$. Equations (4) then look like:

$$|(\underline{v}_a C_a) \cdot X| = 1 \quad (8a)$$
$$|(\underline{v}_b C_b) \cdot X| = 1 \quad (8b)$$
$$|(\underline{v}_c C_c) \cdot X| = 1 \quad (8c)$$

where the matrix elements of the 3×3 matrices $C_a$, $C_b$ and $C_c$ are arrays of polynomial coefficients and X is an array of corresponding products of powers of x, y and z. Note that the domain of validity of this polynomial representation generally is a restricted volume adjacent to the radiators, such as space 39.

Another way to obtain the inverse matrices is empirically. Object 10 is moved successively among the N calibration points $\underline{r}_n$. At each calibration point, object 10 is pointed so that sensor 12 is oriented, first in the +x direction, then in the +y direction, and finally in the +z direction. At each orientation of object 10, the transmitters that contribute to $B_a$, $B_b$ and $B_c$ are excited successively. So, for example, with object 10 at position $\underline{r}$ and pointed so that sensor 12 is oriented in the +x direction, exciting the transmitter that generates the first column of $B_a$ produces a signal in reception circuitry 18 that is equal to the x-component of the first column of $B_a(\underline{r})$, multiplied by k. In this manner $kB_a$, $kB_b$ and $kB_c$ are measured at all N calibration points $\underline{r}_n$, and then are inverted to give the inverse matrices.

Alternatively, the empirical method of obtaining the inverse matrices is effected using a calibration object with all three orthogonal sensors 12, 14 and 16. At each calibration point, the calibration object is pointed so that sensor 12 is oriented in the +x direction, sensor 14 is oriented in the +y direction, and sensor 16 is oriented in the +z direction. At each calibration point, the transmitters that contribute to $B_a$, $B_b$ an $B_c$, are excited successively.

Figure 5:
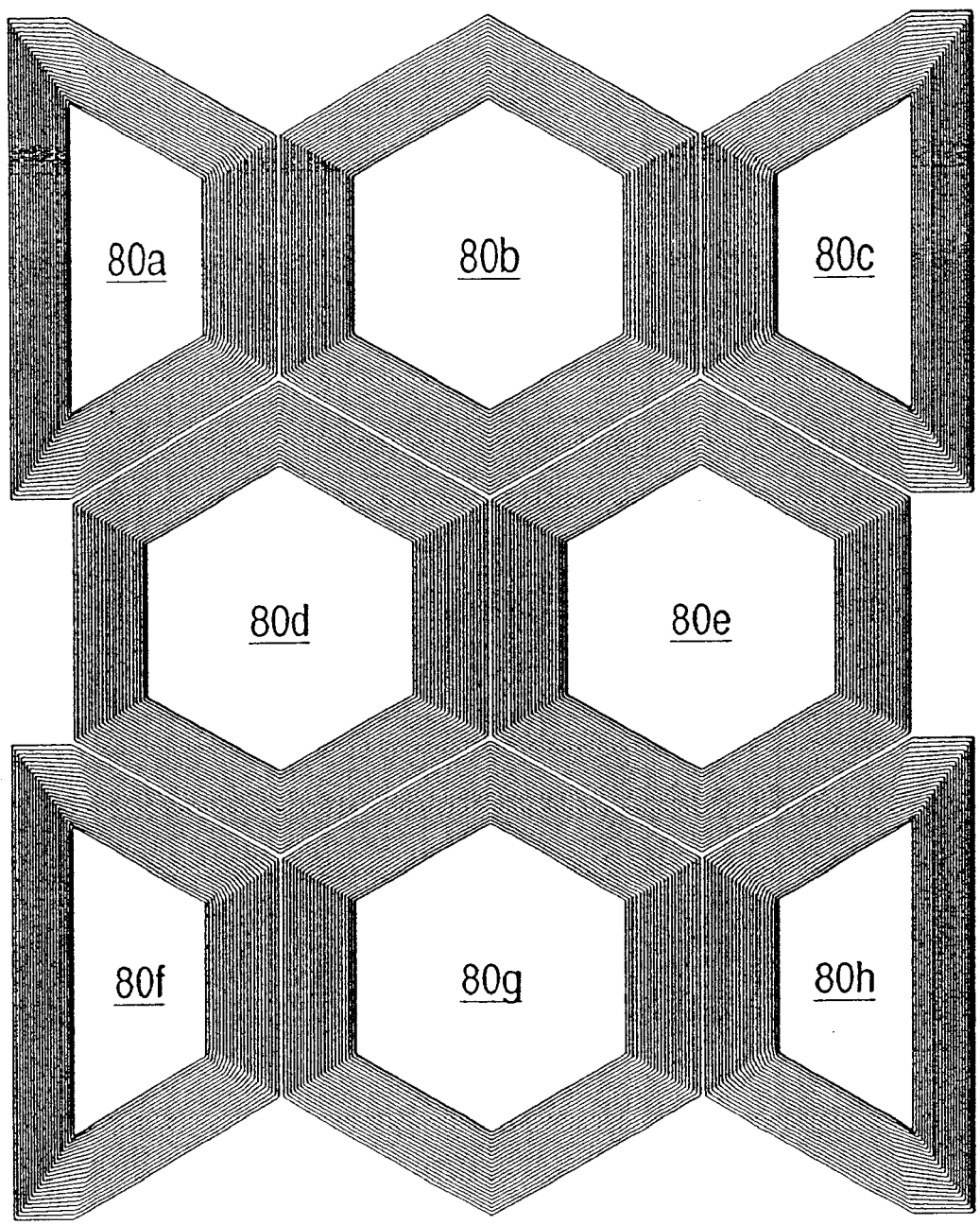
FIG. 5 shows a set of radiators for tracking a moving object that is equipped with both a single sensor and a set of three orthogonal sensors.

Most preferably, the antennas used to generate the magnetic fields are chosen to minimize the polynomial order that gives adequate numerical accuracy. For example, the antennas taught by Gilboa in U.S. Pat. No. 5,853,327 and illustrated in FIG. 13 of that patent, and the antennas taught by Gilboa et al. in WO 00/10456 (which is incorporated by reference for all purposes as if fully set forth herein) and illustrated in FIG. 6 of that PCT application, generate magnetic fields that can be represented by low order polynomials, as illustrated in FIG. 14 of U.S. Pat. No. 5,853,327. Another set of eight antennas 80 that minimize the polynomial order is shown in FIG. 5. With such antennas, polynomials of fifth order, with 56 coefficients $C_{jkl}$ each, are adequate. Note that the minimal radiator set illustrated in FIG. 3 is in fact antennas 80a through 80e.

Figure 6:
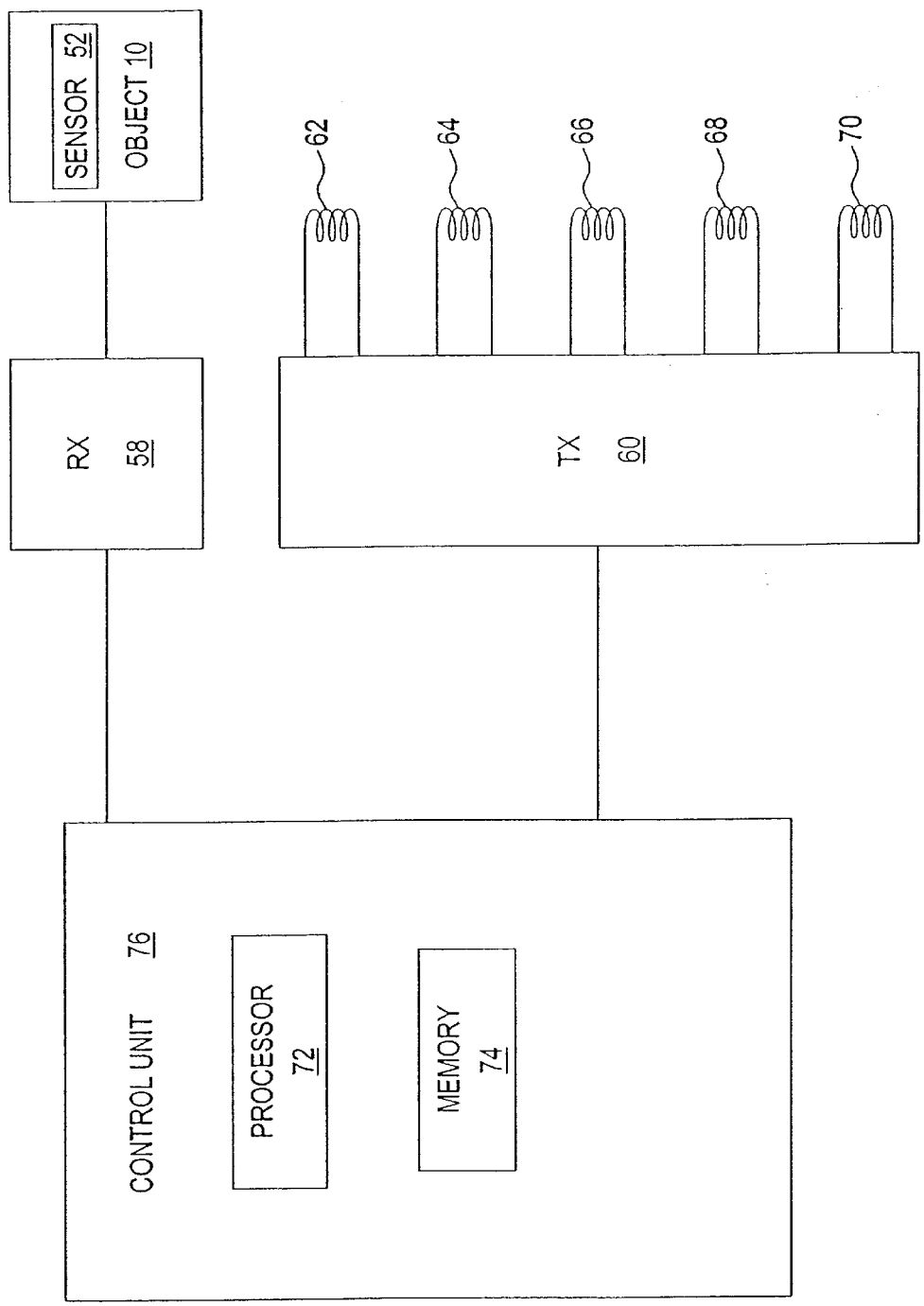
FIGS. 6 and 11 are schematic block diagrams of systems of the present invention.

Antennas 80 have the further advantage of allowing the convenient use of both a single magnetic field component sensor and a three-component sensor in object 10. As described in WO 00/10456, the antennas of FIG. 6 of that PCT application are energized to produce magnetic fields that are symmetric, antisymmetric horizontally as seen in FIG. 6 of that PCT application, or antisymmetric vertically as seen in FIG. 6 of that PCT application, or, most preferably, magnetic fields that can be combined linearly to produce total magnetic fields of such symmetries. In the present case, running direct electrical current in all eight antennas 80 in a common (clockwise or anticlockwise) direction produces a symmetric total DC magnetic field; running electrical current in antennas 80*a*, 80*d* and 80*f* in one direction and in antennas 80*c*, 80*e* and 80*h* in the opposite direction produces a total DC magnetic field that is horizontally antisymmetric as seen in FIG. 5; and running electrical current in antennas 80*a*, 80*b* and 80*c* in one direction and in antennas 80*f*, 80*g* and 80*h* in the opposite direction produces a total DC magnetic field that is vertically antisymmetric as seen in FIG. 5. Similarly, running alternating electrical current in all eight antennas 80 with a common phase produces a symmetric total AC magnetic field, running alternating electrical current in antennas 80*c*, 80*e* and 80*h* with a phase opposite to the phase of alternating electrical current in antennas 80*a*, 80*d* and 80*f* produces a total AC magnetic field that is horizontally antisymmetric as seen in FIG. 5; and running alternating electrical current in antennas 80*f*, 80*g* and 80*h* with a phase opposite to the phase of alternating electrical current in antennas 80*a*, 80*b* and 80*c* produces a total AC magnetic field that is vertically antisymmetric as seen in FIG. 5. As in the case of the antennas of FIG. 6 of WO 00/10456, it is most preferable to combine received fields mathematically in a manner that emulates the receipt of symmetric, horizontally antisymmetric and vertically antisymmetric transmitted fields.

The antennas of FIG. 4 may be used similarly in conjunction with an object 10 that bears both a single magnetic field component sensor and a three-component sensor. With coils 40, 40', 40", 42, 42', 42", 44, 44' and 44" used successively as transmitters, let the total field magnitudes measured by the three-component sensor at any particular position of object 10 be $M_{40}$, $M_{40'}$, $M_{40''}$, $M_{42}$, $M_{42'}$, $M_{42''}$, $M_{44}$, $M_{44'}$ and $M_{44''}$, respectively. Let $L_{40}=\log(M_{40}+M_{40'}+M_{40''})$, $L_{42}=\log(M_{42}+M_{42'}+M_{42''})$ and $L_{44}=\log(M_{44}+M_{44'}+M_{44''})$. These three expressions are approximately proportional to the distance of object 10 from antenna sets a, b and c, respectively. Then the most suitable inputs to a polynomial operator for computing the position of object 10 from these measurements are the following three expressions: two normalized antisymmetric expressions:

$$\frac{L_{42}-L_{40}}{L_{42}+L_{40}}$$

$$\frac{L_{44}-\frac{L_{40}+L_{42}}{2}}{L_{44}+\frac{L_{40}+L_{42}}{2}}$$

and one unnormalized symmetric expression:

$$L_{40}+L_{42}+L_{44}$$

Given the position of object 10, the orientation of object 10 is obtained from the single-component sensor measurements as described above.

Whether the polynomial coefficients $C_{jkl}$ (or, equivalently, the polynomial coefficient matrices C) are determined theoretically or empirically, these coefficients are parameters of equations (4) (or of equations (8)) that relate the signals received by reception circuitry 18 from sensor 12 to the position $\underline{r}$ of object 10. These equations are solved by standard methods for solving nonlinear equations. See, for example, William H. Press et al., *Numerical Recipes in C* (Cambridge, 1992), chapter 9. With the position $\underline{r}$ of object 10 determined, equations (3) become three simultaneous linear equations for $R_{11}$, $R_{12}$ and $R_{13}$; and the YAW and PITCH of object 10 are simple inverse trigonometric functions of $R_{11}$, $R_{12}$ and $R_{13}$.

The case of two magnetic field sensors on object 10 is handled similarly. Polynomial expressions for $B^{-1}k^{-1}$ are determined either theoretically or experimentally. Equations (6) are solved for the position $\underline{r}$ of object 10. If desired, equations (5*a*), (5*b*) and (6*c*) are solved for all three orientation angles (YAW, PITCH and ROLL) of object 10.

In the case of empirically determined parameters, the scope of the present invention also includes the use of three or more sensors on object 10. The prior art does not teach the use of empirically determined parameters in equations such as equations (4) for locating a moving object, even when three or more sensors are used.

FIG. 6 is a schematic block diagram of a system of the present invention for tracking moving object 10 using a single vector field sensor 52 that supplies signals to reception circuitry 58. As noted above, vector field sensor 52 may be a coil of electrically conductive wire, in the manner of sensors 12, 14 and 16, for sensing quasistatic magnetic fields, or one of the single component magnetometers listed above, for sensing static magnetic fields. The vector fields are generated using five vector field radiators 62, 64, 66, 68 and 70. Antennas 30, 32, 34, 36 and 38 are examples of vector field radiators 62, 64, 66, 68 and 70 in the case of the vector fields being static or quasistatic magnetic fields. Radiators 62, 64, 66, 68 and 70 are excited using transmission circuitry 60. Transmission circuitry 60 and reception circuitry 58 are under the overall control of a control unit 76 that includes a memory 74 for storing coefficients $C_{jkl}$ and a processor 72 for solving equations (4).

Figure 7:
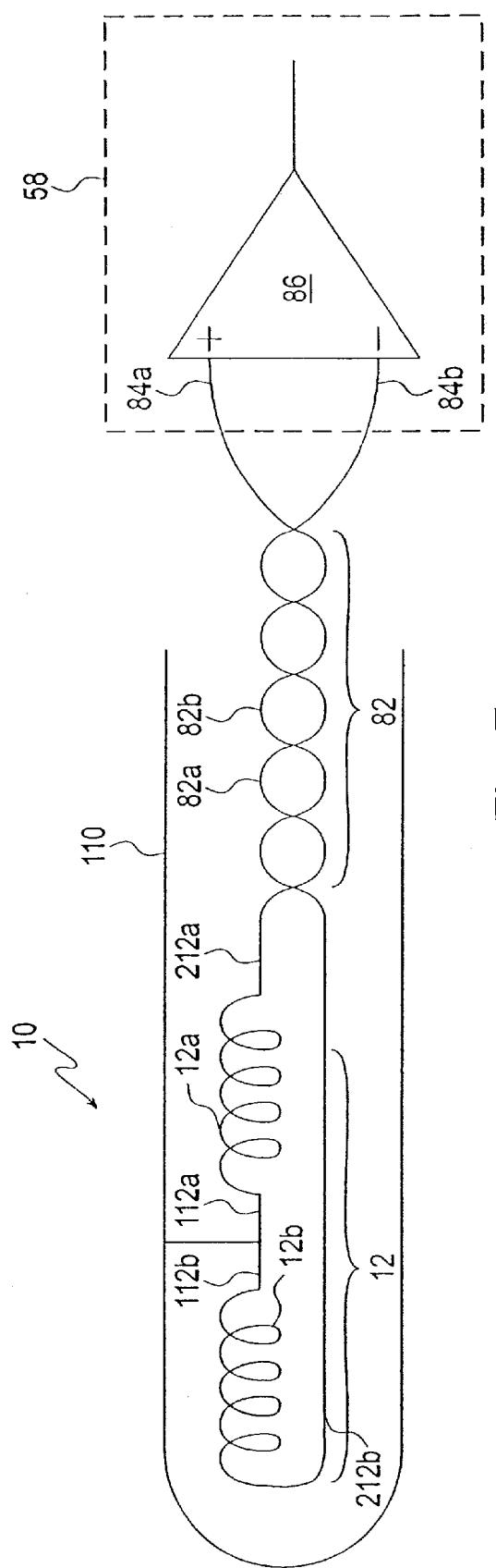
FIG. 7 shows a preferred single sensor coil of the present invention and some of the associated electronics.

Generally, the hardware described in WO 00/10456 is applicable, mutatis mutandis, to the present invention. FIG. 7 shows a preferred configuration of a sensor coil 12 mounted within an elongated object 10 that has an electrically conducting outer housing 110, and that is configured to suppress electromagnetic coupling. Specifically, sensor coil 12 has two subcoils, 12*a* and 12*b*, connected in series by inner leads 112*a* and 112*b* thereof. An outer lead 212*a* of subcoil 12*a* is connected by a wire 82*a* of a twisted wire pair 82 to a positive input 84*a* of a differential amplifier 86 of reception circuitry 58. An outer lead 212*b* of subcoil 12*b* is connected by a wire 82*b* of twisted wire pair 82 to a negative input 84*b* of differential amplifier 86. Inner leads 112*a* and 112*b* also are grounded to outer housing 110, as shown.

According to another aspect of the present invention, the sensor coil or coils of the present invention are integrated into a guide wire such as is used to aid in the insertion of a catheter into the body of a medical or veterinary patient and to evaluate the body cavity (for example a blood vessel) through which the catheter will travel. In general, a guide wire is inserted into a body system such as a blood vessel and the vessel is probed with the guide wire. The catheter is slipped over the guide wire and the guide wire is withdrawn. The catheter is then eased through the vessel to the desired location.

To position the guide wire at a particular location within the body, it is useful to have a means of detecting the location of the distal tip of the guide wire. To that end, Owens et al., in U.S. Pat. No. 5,386,828, which is incorporated by reference for all purposes as if fully set forth herein, teach a guide wire assembly that includes a helical guide wire and a separate sensor coil in the central channel or lumen of the guide wire. In the guide wire assembly of the present invention, the sensor coil or coils are formed integrally as portions of the guide wire itself.

FIGS. 8A and 8B illustrate one such guide wire 300 of the present invention. FIG. 8A is an external view of guide wire 300. FIG. 8B is a cut away view of guide wire 300. Guide wire 300 consists of a helical coil 302 that is wound about a longitudinal axis 314 of a central channel 312 and that is capped on the distal end thereof by a hemispherical cap 304. Coil 302 includes a distal portion 306, a medial portion 308 and a proximal portion 310. Portions 306, 308 and 310 are in tandem, meaning that these portions are situated successively along axis 314. Ellipses ( . . . ) indicate that proximal portion 310 continues to the left. Distal portion 306 and proximal portion 310 are made of an electrically conducting material, preferably a metal such as copper, silver, gold, platinum, palladium or the like, most preferably copper. The electrically conducting portions of helical coil 302, i.e., distal portion 306 and proximal portion 310 preferably are coated with an electrical insulator, such as a thin layer of polyurethane. Medial portion 308 is made of an electrical insulator, as indicated by the shading of medial portion 308. Distal portion 306 constitutes a sensor coil for sensing a magnetic field component of a quasistatic electromagnetic field. A first electrically conducting wire 316 is electrically coupled, for example by soldering, to a distal end 320 of distal portion 306. Wire 316 runs, substantially parallel to axis 314, towards the proximal end of guide wire 300. A second electrically conducting wire 318 is electrically coupled, for example by soldering, to a proximal end 322 of distal portion 306. Wire 318 runs, substantially parallel to axis 314, towards the proximal end of guide wire 300. In the portion of channel 312 that is defined by medial portion 308 and proximal portion 310 of coil 302, wires 316 and 318 form a twisted pair. In a system of the present invention, wires 316 and 318 lead to reception circuitry such as reception circuitry 58.

Figure 9:
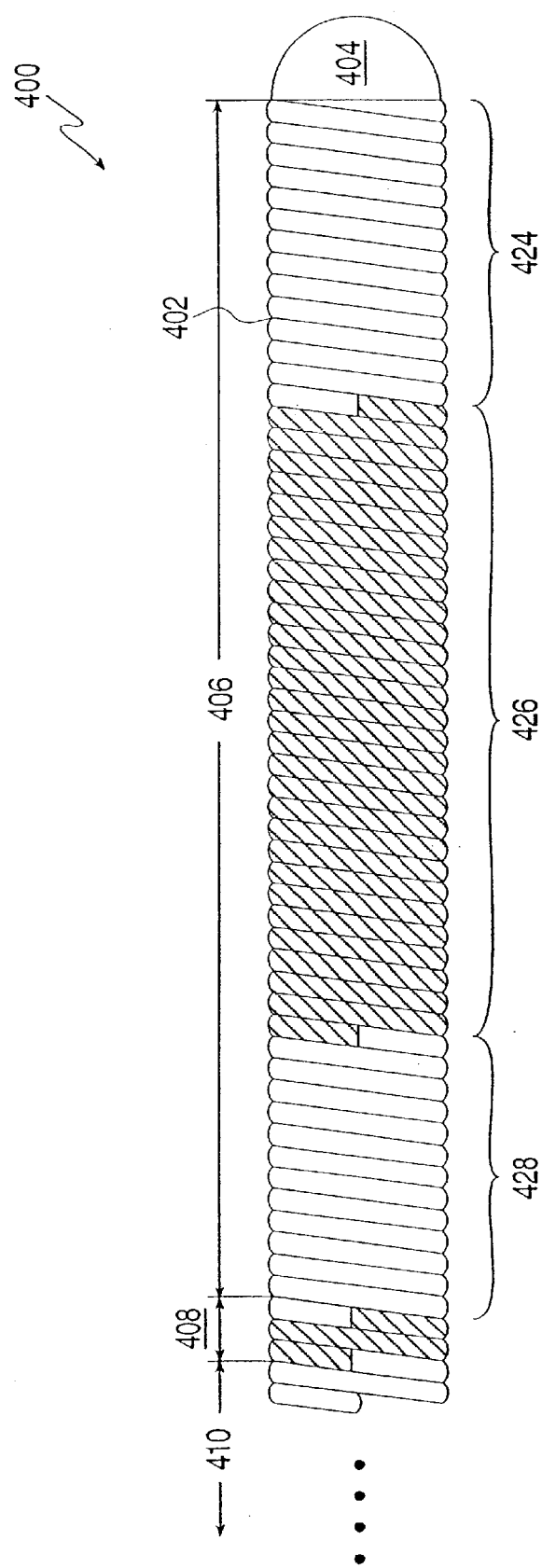

FIG. 9 illustrates another such guide wire 400 of the present invention. Guide wire 400 consists of a helical coil 402 that is capped on the distal end thereof by a hemispherical cap 404. Like guide wire 300, guide wire 400 includes a distal portion 406, a medial portion 408 and a proximal portion 410, all in tandem. The ellipsis indicates that proximal portion 410 continues to the left. Like proximal portion 310 of guide wire 300, proximal portion 410 of guide wire 400 is made of an electrically conducting material. Like medial portion 308 of guide wire 300, medial portion 408 of guide wire 400 is made of an electrical insulator. Unlike distal portion 306 of guide wire 300, distal portion 406 of guide wire 400 includes three sections in tandem: an electrically conducting distal section 424, an electrically insulating medial section 426 and an electrically conducting proximal section 428. Electrically conducting section 424 and 428 constitute sensor coils for sensing respective magnetic field components of a quasistatic electromagnetic field. As in the case of guide wire 300, in a system of the present invention, electrically conducting sections 424 and 428 are connected to reception circuitry such as reception circuitry 58 by respective twisted wire pairs.

If distal portion 406 is sufficiently long to be significantly flexible, and if medial section 426 is relatively long compared to distal section 424 and proximal section 428, then the measured positions and orientations of distal section 424 and proximal section 428 indicate both the location of distal portion 406 and the extent to which distal portion 406 is bent. If distal portion 406 is relatively short, so that distal section 424 and proximal section 428 always are nearly aligned with each other, then distal section 424 and proximal section 428 preferably are connected as illustrated in FIG. 7 to provide a single sensor coil. Because of the inherent flexibility of coil 402, distal section 424 and proximal section 428 in general are not exactly aligned with each other. Consequently, the orientation that is measured using distal section 424 and proximal section 428 in the configuration of FIG. 7 is an average orientation of distal portion 406.

Figure 10:
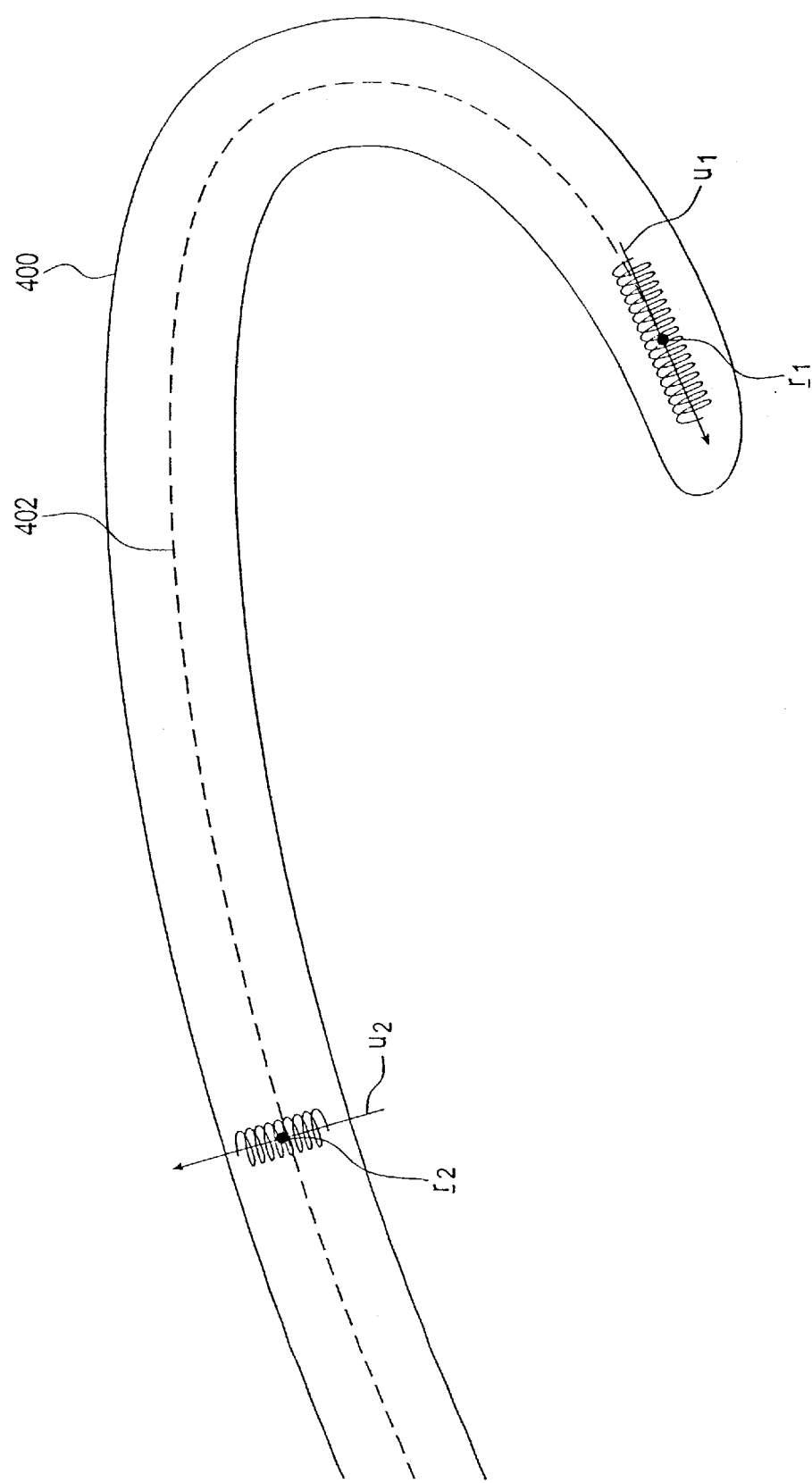

To position a guide wire at a particular location within the body, it also is useful to have a means of detecting the degree to which the guide wire is bent and twisted. FIG. 10 illustrates, schematically, a guide wire 400 of the present invention, the distal portion whereof is equipped with two sensor coils 404 and 406. Sensor coil 404, at the distal tip of guide wire 400, is substantially parallel to longitudinal axis 402 of guide wire 400. Sensor coil 406 is positioned proximal of sensor coil 404 and is substantially perpendicular to axis 402. The present invention measures the position ($\underline{r}_2$) of the center of coil 404, as well as a unit vector $\hat{u}_1$ that points in the direction of the axis of coil 404. The present invention also measures the position ($\underline{r}_2$) of the center of coil 406, as well as a unit vector $\hat{u}_2$ that points in the direction of the axis of coil 406. Assuming that the distal portion of guide wire 400 is bent in a circle, this circle is fully determined by position vectors $\underline{r}_1$ and $\underline{r}_2$ and by unit vector $\hat{u}_1$. Note that unit vector $\hat{u}_1$ is tangent to the circle. Unit vector $\hat{u}_2$ then determines the degree to which guide wire 400 is twisted.

Figure 11:
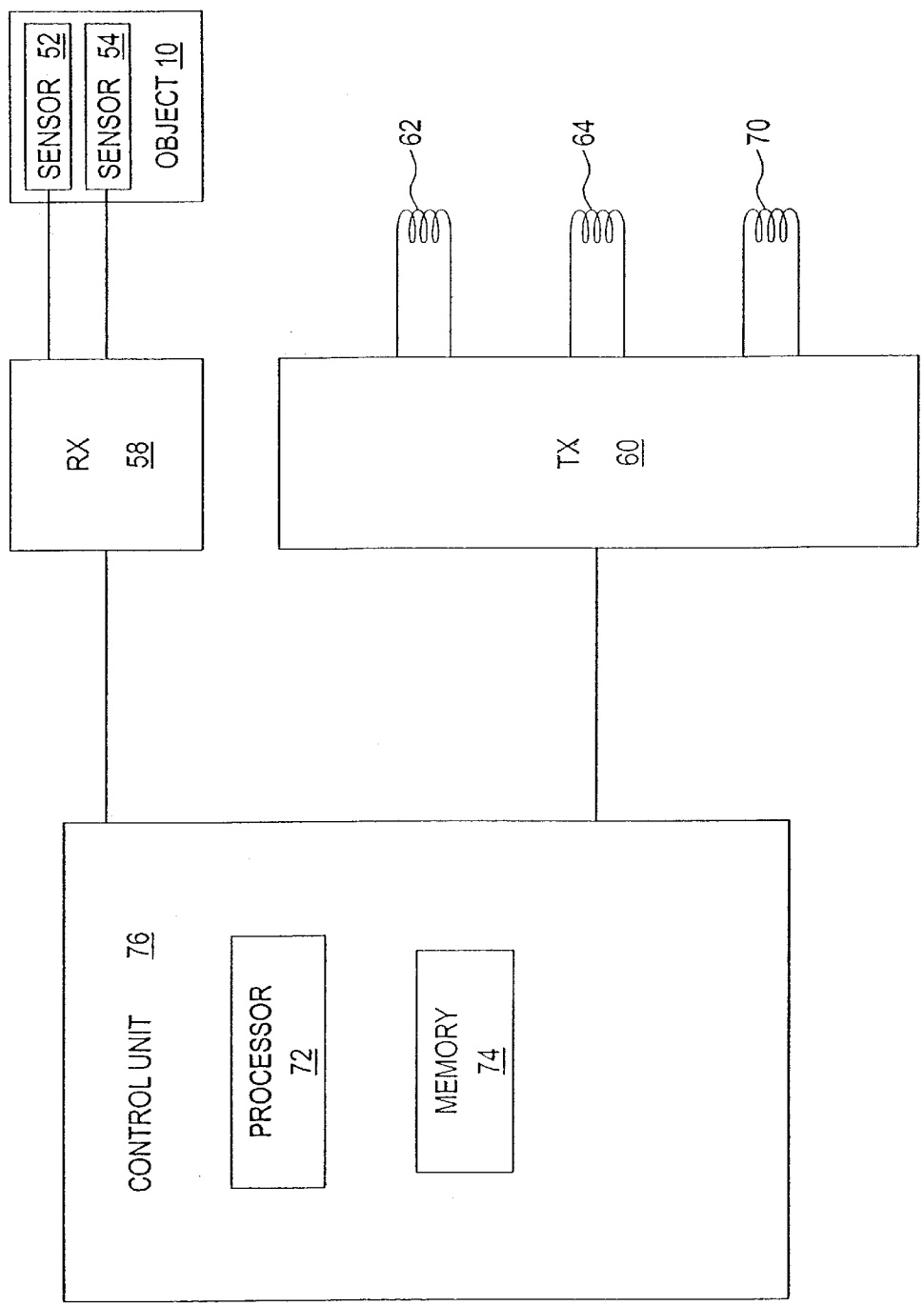

FIG. 11 is a schematic block diagram of a system of the present invention for tracking moving object 10 using two vector field sensors 52 and 54. The system of FIG. 11 is almost identical to the system of FIG. 6, the two main differences being that the system of FIG. 11 includes two vector field sensors 52 and 54 but only three vector field radiators 62, 64 and 66.

While the invention has been described with respect to a limited number of embodiments, it will be appreciated that many variations, modifications and other applications of the invention may be made.

What is claimed is:

1. A method of tracking an object that moves in three dimensions, comprising the steps of:
   (a) providing the object with at least one vector field component sensor for measuring a respective component of a vector field;
   (b) for each said at least one vector field component sensor, empirically determining parameters of a set of equations that relate said respective component only to a position of the object with respect to a reference frame;
   (c) providing a plurality of vector field generators for generating respective instances of said vector field, each said generator having a fixed respective position in said reference frame;
   (d) for each said generator:
      (i) generating said respective instance of said vector field, and
      (ii) for each said at least one sensor, measuring said respective component of said respective instance of said vector field; and
   (e) solving said set of equations for said position of the object.

2. The method of claim 1, wherein said vector field is a magnetic field.

3. The method of claim 2, wherein each said at least one sensor includes at least one loop of an electrical conductor.

4. The method of claim 2, wherein each said at least one sensor includes a single-component magnetometer.

5. The method of claim 2, wherein each said generator includes a radiator of said respective instance of said vector field, each said radiator including at least one loop of an electrical conductor.

6. The method of claim 1, wherein said generators are mutually independent.

7. The method of claim 1, wherein each said generator includes a radiator of said respective instance of said vector field, at least one of said radiators being spatially extended.

8. The method of claim 1, wherein the object is provided with at most two said sensors.

9. The method of claim 8, wherein at least three said vector field generators are provided.

10. The method of claim 8, wherein the object is provided with exactly one said sensor.

11. The method of claim 10, wherein at least five said vector field generators are provided, and wherein said generating of said instances of said vector fields includes generating three independent groups of said instances, each said group including three said instances.

12. The method of claim 1, wherein said equations are polynomials in coordinates of said position of the object, said parameters of said equations being coefficients of said polynomials.

13. The method of claim 1, further comprising the step of:
(f) computing an orientation of the object with respect to said reference frame.

14. A method of tracking an object that moves in three dimensions, comprising the steps of:
(a) providing the object with at most two vector field component sensors for measuring respective components of a vector field;
(b) for each said at most two vector field component sensors, determining parameters of a set of equations that relate said respective component only to a position of the object with respect to a reference frame;
(c) providing at least three vector field generators for generating respective instances of said vector field, each said generator having a fixed respective position in said reference frame;
(d) for each said generator:
(i) generating said respective instance of said vector field, and
(ii) for each said at most two sensors, measuring said respective component of said respective instance of said vector field; and
(e) solving said set of equations for said position of the object.

15. The method of claim 14, wherein said vector field is a magnetic field.

16. The method of claim 15, wherein each said sensor includes at least one loop of an electrical conductor.

17. The method of claim 15, wherein each said sensor includes a single-component magnetometer.

18. The method of claim 15, wherein each said generator includes a radiator of said respective instance of said vector field, each said radiator including at least one loop of an electrical conductor.

19. The method of claim 14, wherein said generators are mutually independent.

20. The method of claim 14, wherein each said generator includes a radiator of said respective instance of said vector field, at least one of said radiators being spatially extended.

21. The method of claim 14, wherein the object is provided with exactly one said sensor.

22. The method of claim 21, wherein at least five said vector field generators are provided, and wherein said generating of said instances of said vector fields includes generating three independent groups of said instances, each said group including three said instances.

23. The method of claim 14, wherein said parameters are determined empirically.

24. The method of claim 14, wherein said parameters are determined theoretically.

25. The method of claim 14, wherein said equations are polynomials in coordinates of said position of the object, said parameters of said equations being coefficients of said polynomials.

26. The method of claim 14, further comprising the step of:
(f) computing an orientation of the object with respect to said reference frame.

27. A system for tracking an object that moves in three dimensions, comprising:
(a) at least one vector field component sensor, associated with the object, for measuring a respective component of a vector field;
(b) a processor for solving a set of equations that relate, for each said at least one sensor, said respective component of said vector field only to a position of the object with respect to a reference frame;
(c) a memory for storing empirically determined parameters of said equations; and
(d) a plurality of vector field generators, having fixed respective positions in said reference frame, for generating respective instances of said vector field.

28. The system of claim 27, including a single said vector field component sensor.

29. The system of claim 28, wherein said single vector field component sensor is included in a distal portion of a guide wire.

30. The system of claim 27, including exactly two said vector field component sensors.

31. The system of claim 30, wherein said two vector field component sensors are in tandem in a distal portion of a guide wire.

32. The system of claim 30, wherein said two vector field component sensors are included in a distal portion of a guide wire, with a first said vector field component sensor being substantially parallel to a longitudinal axis of said guide wire and a second said vector field component sensor being substantially perpendicular to said axis.

33. A system for tracking an object that moves in three dimensions, comprising:
(a) at most two vector field component sensors, associated with the object, for measuring respective components of a vector field;
(b) a processor for solving a set of equations that relate, for each said sensor, said respective component of said vector field only to a position of the object with respect to a reference frame;
(c) a memory for storing parameters of said equations; and
(d) at least three vector field generators, having fixed respective positions in said reference frame, for generating respective instances of said vector field.

34. The system of claim 33, including a single said vector field component sensor.

35. The system of claim 34, wherein said single vector field component sensor is included in a distal portion of a guide wire.

36. The system of claim 33, including exactly two said vector field component sensors.

37. The system of claim 36, wherein said two vector field component sensors are in tandem in a distal portion of a guide wire.

38. The system of claim 36, wherein said two vector field component sensors are included in a distal portion of a guide wire, with a first said vector field component sensor being substantially parallel to a longitudinal axis of said guide wire and a second said vector field component sensor being substantially perpendicular to said axis.

39. A method of tracking an object that moves in three dimensions, comprising the steps of:
(a) providing the object with at least one vector field component sensor for measuring a respective component of a vector field;
(b) empirically determining a rotationally invariant operator that relates said at least one respective component to a position of the object with respect to a reference frame;
(c) providing a plurality of vector field generators for generating respective instances of said vector field, each said generator having a fixed respective position in said reference frame;
(d) for each said generator:
(i) generating said respective instance of said vector field, and
(ii) for each said at least one sensor, measuring said respective component of said respective instance of said vector field; and
(e) computing said position of the object, using said operator.

40. A method of tracking an object that moves in three dimensions, comprising the steps of:
(a) providing the object with at most two vector field component sensors for measuring respective components of a vector field;
(b) determining a rotationally invariant operator that relates said at most two respective components to a position of the object with respect to a reference frame;
(c) providing at least three vector field generators for generating respective instances of said vector field, each said generator having a fixed respective position in said reference frame;
(d) for each said generator:
(i) generating said respective instance of said vector field, and
(ii) for each said at most two sensors, measuring said respective component of said respective instance of said vector field; and
(e) computing said position of the object, using said operator.

41. A system for tracking an object that moves in three dimensions, comprising:
(a) at least one vector field component sensor, associated with the object, for measuring a respective component of a vector field;
(b) a memory for storing an empirically determined, rotationally invariant operator that relates said at least one respective component of said vector field to a position of the object with respect to a reference frame;
(c) a processor for computing said position, using said operator; and
(d) a plurality of vector field generators, having fixed respective positions in said reference frame, for generating respective instances of said vector field.

42. A system for tracking an object that moves in three dimensions, comprising:
(a) at most two vector field component sensors, associated with the object, for measuring respective components of a vector field;
(b) a memory for storing a rotationally invariant operator that relates said at most two respective components of said vector field to a position of the object with respect to a reference frame;
(c) a processor for computing said position, using said operator; and
(d) at least three vector field generators, having fixed respective positions in said reference frame, for generating respective instances of said vector field.

43. A method of tracking an object that moves in three dimensions, comprising the steps of:
(a) providing the object with at most two vector field component sensors for measuring respective components of a vector field;
(b) for each said at most two vector field component sensors, determining parameters of a set of equations that relate said respective component to a position of the object with respect to a reference frame, independent of an orientation of the object;
(c) providing at least three vector field generators for generating respective instances of said vector field, each said generator having a fixed respective position in said reference frame;
(d) for each said generator:
(i) generating said respective instance of said vector field, and
(ii) for each said at most two sensors, measuring said respective component of said respective instance of said vector field; and
(e) solving said set of equations for said position of the object.

44. A system for tracking an object that moves in three dimensions, comprising:
(a) at most two vector field component sensors, associated with the object, for measuring respective components of a vector field;
(b) a processor for solving a set of equations that relate, for each said sensor, said respective component of said vector field to a position of the object with respect to a reference frame, independent of an orientation of the object;
(c) a memory for storing parameters of said equations; and
(d) at least three vector field generators, having fixed respective positions in said reference frame, for generating respective instances of said vector field.

45. The system of claim 29, wherein said distal portion of said guide wire is substantially helical, and wherein said guide wire also includes a substantially helical, electrically insulating medial portion, said single vector field component sensor being an electrically conducting section of said distal portion of said guide wire.

46. The system of claim 45, wherein said distal portion of said guide wire includes a plurality of said electrically conducting sections, each pair of successive said electrically conducting sections having therebetween an electrically insulating section in tandem with said each pair of successive electrically conducting sections.

47. The system of claim 45, wherein said guide wire further includes a substantially helical, electrically conducting proximal portion in tandem with said medial portion.

48. The system of claim 45, wherein said guide wire further includes a first electrically conducting wire, electrically coupled to a distal end of said distal portion of said guide wire, and wherein said guide wire further includes a second electrically conducting wire, electrically coupled to a proximal end of said distal portion of said guide wire.

49. The system of claim 48, wherein said distal and medial portions of said guide wire define an axial channel, wherethrough said electrically conducting wires extend.

50. The system of claim 31, wherein said distal portion of said guide wire is substantially helical, said two vector field component sensors being electrically conducting sections of said distal portion of said guide wire that have therebetween an electrically insulating section in tandem with said two electrically conducting sections.

51. The system of claim 50, wherein said guide wire further includes a substantially helical, electrically insulating medial portion in tandem with said distal portion of said guide wire.

52. The system of claim 50, wherein said guide wire further includes a substantially helical, electrically conducting proximal portion in tandem with said medial portion.

53. The system of claim 51, wherein said guide wire further includes a first electrically conducting wire, electrically coupled to a distal end of said distal portion of said guide wire, and wherein said guide wire further includes a second electrically conducting wire, electrically coupled to a proximal end of said distal portion of said guide wire.

54. The system of claim 53, wherein said distal and medial portions of said guide wire define an axial channel, wherethrough said electrically conducting wires extend.

55. The system of claim 35, wherein said distal portion of said guide wire is substantially helical, and wherein said guide wire also includes a substantially helical, electrically insulating medial portion, said single vector field component sensor being an electrically conducting section of said distal portion of said guide wire.

56. The system of claim 55, wherein said distal portion of said guide wire includes a plurality of said electrically conducting sections, each pair of successive said electrically conducting sections having therebetween an electrically insulating section in tandem with said each pair of successive electrically conducting sections.

57. The system of claim 55, wherein said guide wire further includes a substantially helical, electrically conducting proximal portion in tandem with said medial portion.

58. The system of claim 55, wherein said guide wire further includes a first electrically conducting wire, electrically coupled to a distal end of said distal portion of said guide wire, and wherein said guide wire further includes a second electrically conducting wire, electrically coupled to a proximal end of said distal portion of said guide wire.

59. The system of claim 58, wherein said distal and medial portions of said guide wire define an axial channel, wherethrough said electrically conducting wires extend.

60. The system of claim 37, wherein said distal portion of said guide wire is substantially helical, said two vector field component sensors being electrically conducting sections of said distal portion of said guide wire that have therebetween an electrically insulating section in tandem with said two electrically conducting sections.

61. The system of claim 60, wherein said guide wire further includes a substantially helical, electrically insulating medial portion in tandem with said distal portion of said guide wire.

62. The system of claim 61, wherein said guide wire further includes a substantially helical, electrically conducting proximal portion in tandem with said medial portion.

63. The system of claim 61, wherein said guide wire further includes a first electrically conducting wire, electrically coupled to a distal end of said distal portion of said guide wire, and wherein said guide wire further includes a second electrically conducting wire, electrically coupled to a proximal end of said distal portion of said guide wire.

64. The system of claim 63, wherein said distal and medial portions of said guide wire define an axial channel, wherethrough said electrically conducting wires extend.

* * * * *